United States Patent [19]

Jegelka et al.

[11] Patent Number: 5,773,622

[45] Date of Patent: Jun. 30, 1998

[54] CONTINUOUS PROCESS FOR THE PREPARATION OF 4-AMINO-2,2,6,6-TETRAMETHYLPIPERIDINE

[75] Inventors: Udo Jegelka; Gerhard Bachstaedter, both of Recklinghausen; Stefan Frentzen, Raesfeld; Guenter Kreilkamp, Marl; Gerhard Thelen, Nottuln, all of Germany

[73] Assignee: Huels Aktiengesellschaft, Marl, Germany

[21] Appl. No.: 758,859

[22] Filed: Dec. 2, 1996

[30] Foreign Application Priority Data

Nov. 30, 1995 [DE] Germany ............... 195 44 599.6

[51] Int. Cl.⁶ ............................................. C07D 211/56
[52] U.S. Cl. ............................. 546/244; 502/337
[58] Field of Search ................... 546/244, 242; 502/69, 527, 337; 585/264

[56] References Cited

U.S. PATENT DOCUMENTS

| | | | |
|---|---|---|---|
| 4,001,250 | 1/1977 | Lantzsch et al. | 546/244 |
| 4,005,208 | 1/1977 | Bender et al. | 514/320 |
| 4,191,683 | 3/1980 | Brunetti et al. | 524/102 |
| 4,210,518 | 7/1980 | Wilson, Jr. et al. | 208/413 |
| 4,429,157 | 1/1984 | Disteldorf et al. | 564/446 |
| 4,490,480 | 12/1984 | Lok et al. | 502/315 |
| 4,923,992 | 5/1990 | Vignali et al. | 546/186 |
| 5,395,972 | 3/1995 | Furutani et al. | 564/446 |
| 5,478,791 | 12/1995 | Baldauf et al. | 502/337 |
| 5,589,596 | 12/1996 | Furutani et al. | 564/446 |

FOREIGN PATENT DOCUMENTS

| | | |
|---|---|---|
| 0 623 585 | 11/1994 | European Pat. Off. . |
| 44 42 990 | 6/1996 | Germany . |
| 62-016461 | 1/1987 | Japan . |
| 2 176 473 | 12/1986 | United Kingdom . |

OTHER PUBLICATIONS

Patent Abstracts of Japan, vol. 11, No. 193, Jun. 20, 1987, JP-A-62 016461, Jan. 24, 1987.
Patent Abstracts of Japan, vol. 10, No. 185, Jun. 27, 1986, JP-A-61 033169, Dec. 17, 1986.
Database WPI, Derwent Publications, AN-138772, SU-A-1 088 304, Nov. 7, 1987.
Schellhorn, B. Justus Leibigs Annalen der Chemie, 1918, vol. 417, pp. 118–125.

*Primary Examiner*—Alan L. Rotman
*Assistant Examiner*—Garth M. Dahlen
*Attorney, Agent, or Firm*—Oblon, Spivak, McClelland, Maier & Neustadt, P.C.

[57] ABSTRACT

A process for the continuous preparation of 4-amino-2,2,6,6-tetramethylpiperidine (TAD), comprising: passing triacetoneamine, ammonia and hydrogen over a catalyst of at least two layers in a reactor, wherein at least one catalyst layer comprises at least one element of the 4th, 5th, or 6th row of the 8th transition group of the Periodic Table or combinations of these metal elements on a suitable support, where the catalyst content with respect to each individual catalytically active element changes independently from the reactor inlet to the reactor outlet.

21 Claims, No Drawings

CONTINUOUS PROCESS FOR THE PREPARATION OF 4-AMINO-2,2,6,6-TETRAMETHYLPIPERIDINE

BACKGROUND OF THE INVENTION

1. Field of the Invention

The present invention relates to a process for the continuous preparation of 4-amino-2,2,6,6-tetramethylpiperidine (TAD) from triacetoneamine (TAA), ammonia and hydrogen in the presence of one or more elements selected from the eighth transition metal group of the Periodic Table as catalyst, where the catalyst is applied to a suitable support and the support has a content gradient of the catalyst in the direction of flow of the reactants.

2. Description of the Background

For large-scale processes for preparing TAD from TAA, the state of the prior art is such that, almost without exception, the processes are carried out batchwise (e.g. JP 86033169, JP 87016461, GB 2176473, SU 1088304, EP 33529, German Application P 44 42 990.8). A great disadvantage of the batch procedure is that it is associated with the regular running-up and running-down steps of individual batches. Because of these process requirements, only low space-time yields can be achieved with increased energy consumption at the same time. In addition, the reactions are generally conducted in solvents such as alcohols or water (e.g. JP 86033169, JP 87016461, GB 2176473, SU 1088304). Further disadvantages of these processes are additional work-up steps such as catalyst filtration and catalyst change, and also removal of solvent by distillation. The additional and regularly occurring workup steps incur high costs and result in environmental pollution. The most important disadvantage of the batch process is the fact that the reactor has to be depressurized each time and the excess ammonia has to be vaporized, while in the case of continuous processes the excess ammonia can largely remain in the reactor. The amount of ammonia which must be handled is thus significantly lower in continuous operation.

In the batch processes, use is customarily made of cobalt or nickel catalysts at pressures of 10–500 bar and temperatures of 70°–200° C. Significant disadvantages in handling are associated with the use of pyrophoric catalysts (EP 33529). Likewise disadvantageous are the very high amounts of catalyst of up to 10% per batch (based on the amount of TAA used) (EP 33529, GB 2176473) which must be used, which results in high catalyst and disposal costs. A further disadvantage is that satisfactory selectivities are often only achievable using cocatalysts such as alkali metal or alkaline earth metal hydroxides (e.g. GB 2176473, SU 1088304).

In contrast to the large number of batch processes, only a small number of continuous processes for preparing TAD from TAA is known. However, as known in the prior art, the continuous procedure leads to no significant improvement in comparison to the batch procedures. For example, as disclosed in EP 33529, pyrophoric catalysts and ammonia excesses of 1:10–1:50 mol/mol are employed. The high amounts of ammonia serve, on the one hand, as a substitute solvent and, on the other hand, are necessary to shift the equilibrium to the product side and to achieve sufficiently high selectivities. Because of catalyst handling requirements and, because of the high ammonia usage, unfavorable energy and raw materials balances remain as disadvantages. Despite the high ammonia usage, the known continuous processes do not lead to a great improvement in the space-time yields: at an LHSV of at most 0.1 $h^{-1}$ based on TAA, only moderate throughputs can be achieved (LHSV=liquid hourly space velocity). A need continues to exist for an improved method of reacting triacetoneamine, ammonia and hydrogen to prepare 4-amino-2,2,6,6-tetramethylpiperidine.

SUMMARY OF THE INVENTION

Accordingly, one object of the invention is to provide a method of synthesis of 4-amino-2,2,6,6-tetramethylpiperidine which overcomes the disadvantages inherent in the batch methodology of low space-time yields, difficult catalyst handling, high ammonia consumption, complicated work-up procedures, high-cost processing, and environmental pollution.

Another object of the invention is to provide a catalyst system of improved effectiveness for the synthesis of 4-amino-2,2,6,6-tetramethylpiperidine.

Briefly, these objects and other objects of the present invention as hereinafter will become more readily apparent can be attained in a continuous method of preparing TAD by passing TAA, ammonia and hydrogen over at least two layers of a catalyst in a reactor, wherein at least one catalyst layer comprises at least one element of the 4th, 5th, or 6th row of the 8th transition metal group of the Periodic Table or combinations of these metal elements on a suitable support, where the catalyst content with respect to each individual catalytically active element changes independently from the reactor inlet to the reactor outlet.

DETAILED DESCRIPTION OF THE PREFERRED EMBODIMENTS

It has now been found that a catalyst system comprising a catalytically active metal(s) comprising one or more elements of the eighth transition metal group of the Periodic Table in a content gradient on a suitable support enables significant improvement in the synthesis of TAD with respect to the reaction conditions of prior art known batch and continuous processes by passing TAA, ammonia and hydrogen over a catalyst system of at least two layers in a reactor, wherein at least one layer comprises one or more elements of the 4th, 5th, or 6th row(s) of the 8th transition metal group of the Periodic Table or combinations thereof as catalytically active metals on a suitable support, where the catalyst metal content with respect to each individual element changes independently from the reactor inlet to the reactor outlet.

The presence of a catalyst gradient on a suitable support in the reactor drastically increases the effectiveness of the system. The LHSV can be increased from the previous 0.1 $h^{-1}$ based on TAA (EP 33529) to 0.6 $h^{-1}$ based on TAA. The gradient is applied such that the TAA/ammonia mixture at the reactor inlet comes into contact with a section of the reactor having a very low catalyst content. The catalyst content increases progressively through the reactor and thus the reactivity increases up to the reactor outlet.

The catalyst bed in the reactor contains at least one element of the eighth transition metal group of the Periodic Table on a support. The contents of the elements of the 4th period on the support increase independently of each other from the reactor inlet to the reactor outlet to values of up to 40%, preferably to values of up to 20% and particularly preferably to values of up to 15%. At the reactor inlet, the contents of the elements of the 4th row are, independently of one another, from 0 to 39%, preferably from 0 to 20% and particularly preferably from 2 to 15%. The contents of the elements of the 5th and/or 6th row (known as platinum metals) on the support increase independently of each other from the reactor inlet to the reactor outlet to values of up to 20%, preferably to values of up to 10% and particularly preferably to values of up to 5%. At the reactor inlet, the contents of the platinum metals on the support are, independently of one another, from 0 to 19%, preferably from 0 to 10% and particularly preferably from 0 to 5%.

Batches of support material having various catalyst contents can be arranged in layers so that there is a stepwise change in the catalyst content. The number of layers can be two or any greater number. In the latter case, a transition from a stepwise change in the catalyst content to a continuous gradient is achieved.

The elements are preferably used in metallic form. Cobalt, nickel, ruthenium, palladium and platinum are preferably employed. The metals can be used per se or after reduction of their oxides, with the use of nonpyrophoric catalysts being preferred. In order to optimize the reactivity gradient, one metal or a mixture of a plurality of metals can be used. In the case of the simultaneous use of elements of the 4th row and elements of the platinum metals, the catalyst content can also decrease in the direction of flow as the catalytically active metal transitions from the elements of the 4th row to the elements of the platinum metals. The use of a gradient achieves high space-time yields at complete conversion.

Matching the reactor temperature to the gradient enables secondary reactions to be very largely suppressed and decompositions to be virtually completely avoided. Thus, it is possible to achieve selectivities of up to >99% based on TAA if the temperatures in the aminative hydrogenation are up to 200° C., preferably from 80° to 170° C. and in particular from 100° C. to 150° C.

The process allows the ammonia consumption to be reduced without impairment of quality from the present TAA:ammonia ratio of up to 1:50 mol/mol to from 1:1 to 1:20 mol/mol, preferably from 1:1 to 1:10 mol/mol and in particular from 1:3 to 1:5 mol/mol.

High catalyst operating lives are achieved with suitable support materials. Of particular importance are hydrothermally resistant aluminum oxides. It is also possible to use various suitable support materials in layers or as mixtures.

The working pressures of the reaction are in the range known in the prior art, viz. from 10 to 500 bar, in particular from 20 to 300 bar.

In this process, it is possible to omit the use of a solvent.

It is possible to employ a multistage procedure and also a plurality of individual reactors connected in series, with the above recited quantities for the catalyst content then applying to the total reactor, i.e. the sum of the individual reactors. However, preference is given to a single-stage process.

The advantage of the process of the invention is based on the substantial improvement in the space-time yield which is achieved by means of the high throughput. This is accompanied by a significant reduction in the production costs as a result of the simple manner in which the continuous, in particular single-stage, process can be carried out. The high operating lives avoid frequent catalyst changes and the catalyst costs are drastically reduced. The work-up is greatly simplified by the solvent-free operation and the very substantial reduction in the consumption of ammonia. Normal distillation procedures are sufficient to purify the product in or to achieve the known (EP 33529) yields and purities.

Having generally described this invention, a further understanding can be obtained by reference to certain specific examples which are provided herein for purposes of illustration only and are not intended to be limiting unless otherwise specified.

EXAMPLES

Example 1

A $0.5M^3$ trickle-mode oven was charged with 340 kg of an aluminum oxide support. The support was coated with a nickel catalyst, with the nickel content rising from 5% at the oven inlet to 14% at the oven outlet. TAA and ammonia were passed through the oven under a hydrogen pressure of 300 bar. At an LHSV of 0.4 $h^{-1}$ of TAA and 0.44 $h^{-1}$ of $NH_3$ (i.e. TAA:$NH_3$=1:7.4 mol/mol) and an oven temperature of 125°–145° C., 96% pure TAD was produced from 97% pure TAA. The product obtained was worked-up by distillation.

Example 2

In a method similar to Example 1, 96% pure TAD was produced from 97% pure TAA in a 500 ml trickle-mode oven at an LHSV of 0.6 $h^{-1}$ of TAA and 0.4 $h^{-1}$ of $NH_3$ (i.e. TAA:$NH_3$=1:4.5 mol/mol), a hydrogen pressure of 285 bar and an oven temperature of 130°–150° C. The product was worked-up by distillation.

Example 3

A 500 ml trickle-mode oven was charged with 400 ml of an aluminum oxide support. The support was coated with a nickel catalyst, with the nickel content increasing from 0% at the oven inlet to 14% at the oven outlet. TAA and ammonia were passed through the oven under a hydrogen pressure of 285 bar. At an LHSV of 0.38 $h^{-1}$ of TAA and 0.25 $h^{-1}$ of $NH_3$ (i.e. TAA:$NH_3$=1:4.4 mol/mol) and an oven temperature of 120°–145° C., 96% pure TAD was produced from 97% pure TAA. The product was worked-up by distillation.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A process for the continuous preparation of 4-amino-2,2,6,6-tetramethylpiperidine (TAD), comprising:
    passing triacetoneamine (TAA), ammonia and hydrogen over a catalyst of at least two layers in a reactor, wherein at least one catalyst layer comprises at least one element of the 4th, 5th, or 6th row of the 8th transition group of the Periodic Table or combinations of these metal elements on a suitable support, where the catalyst content with respect to each individual catalytically active element changes independently from the reactor inlet to the reactor outlet.

2. The process as claimed in claim 1, wherein the catalyst contents of the elements of the 4th row on the support increase independently of each other from the reactor inlet to the reactor outlet to values of up to 40%.

3. The process as claimed in claim 2, wherein the amount of catalytically active metal ranges up to 20%.

4. The process as claimed in claim 3, wherein said amount of metal ranges up to 15%.

5. The process as claimed in claim 1, wherein, at the reactor inlet, the catalyst contents of the elements of the 4th row on the support range, independently of each other, from 0 to 39%.

6. The process as claimed in claim 5, wherein said content ranges from 0 to 20%.

7. The process as claimed in claim 6, wherein said content ranges from 2 to 15%.

8. The process as claimed in claim 1, wherein the catalyst content of the elements of the 5th and/or 6th row on the support increase independently of each other from the reactor inlet to the reactor outlet to values of up to 20%.

9. The process as claimed in claim 8, wherein the catalyst content of each element ranges up to 10%.

10. The process as claimed in claim 9, wherein the catalyst content of each element ranges up to 5%.

11. The process as claimed in claim 1, wherein, at the reactor inlet, the catalyst contents of the elements of the 5th and/or 6th row on the support, independently of each other, range from 0 to 19%.

12. The process as claimed in claim 11, wherein said catalyst content ranges from 0 to 10%.

13. The process as claimed in claim 12, wherein said catalyst content ranges from 0 to 5%.

14. The process as claimed in claim 1, wherein the reaction is conducted at a reactor temperature of up to 200° C.

15. The process as claimed in claim 14, wherein said temperature ranges from 80° to 170° C.

16. The process as claimed in claim 15, wherein said temperature ranges from 100° C. to 150° C.

17. The process as claimed in claim 1, wherein the molar ratio TAA:ammonia ranges from 1:1 to 1:20 mol/mol.

18. The process as claimed in claim 17, wherein said molar ratio ranges from 1:1 to 1:10 mol/mol.

19. The process as claimed in claim 18, wherein said molar ratio ranges from 1:3 to 1:5 mol/mol.

20. The process as claimed in claim 1, wherein said catalytically active metal is cobalt, nickel, ruthenium, palladium or platinum or mixtures thereof.

21. The process as claimed in claim 1, wherein, when the catalyst layers are formed from several metals of the 4th row in the platinum metals, the distribution of the metals in the layers is such that, in the direction of flow of the reactants through the catalyst layers in the reactor, the metal content of the 4th row elements increases while the platinum metal content increases.

* * * * *